United States Patent [19]

Kurer

[11] Patent Number: 4,726,770

[45] Date of Patent: Feb. 23, 1988

[54] TOOTH RESTORATION AND MEANS FOR USE THEREIN

[76] Inventor: Hans G. Kurer, 6 Blenheim Close, Hale, Altrincham, Cheshire WA15 2RU, England

[21] Appl. No.: 824,462

[22] Filed: Jan. 31, 1986

[30] Foreign Application Priority Data

Jan. 12, 1985 [GB] United Kingdom ............... 8500801
Feb. 8, 1985 [GB] United Kingdom ............... 8503267

[51] Int. Cl.$^4$ ............................................. A61C 5/04
[52] U.S. Cl. ................................. 433/229; 433/215; 433/39
[58] Field of Search ................. 433/149, 40, 49, 39

[56] References Cited

U.S. PATENT DOCUMENTS

| | | | |
|---|---|---|---|
| 4,234,310 | 11/1980 | Leuthard | 433/228.1 |
| 4,514,174 | 4/1985 | Dougherty | 433/228.1 |
| 4,553,936 | 11/1985 | Wang | 433/229 |
| 4,608,021 | 8/1986 | Barrett | 433/229 |

Primary Examiner—Robert Peshock
Attorney, Agent, or Firm—Fisher, Christen & Sabol

[57] ABSTRACT

A method of and means for tooth restoration is disclosed wherein an inclusion, in the form of a preformed body (11) utilized in the creation of a contact point with an adjacent tooth, the body, which body has a profiled knuckle-forming surface thereto, being positioned in the tooth cavity and being held in pressure contact with a matrix band while the cavity is filled with composite resin so as at least partially to embed the body therein, as the resin is cured or set, the arrangement being such that, on setting or curing of the resin, the body is maintained in position in pressure contact with the matrix band.

18 Claims, 5 Drawing Figures

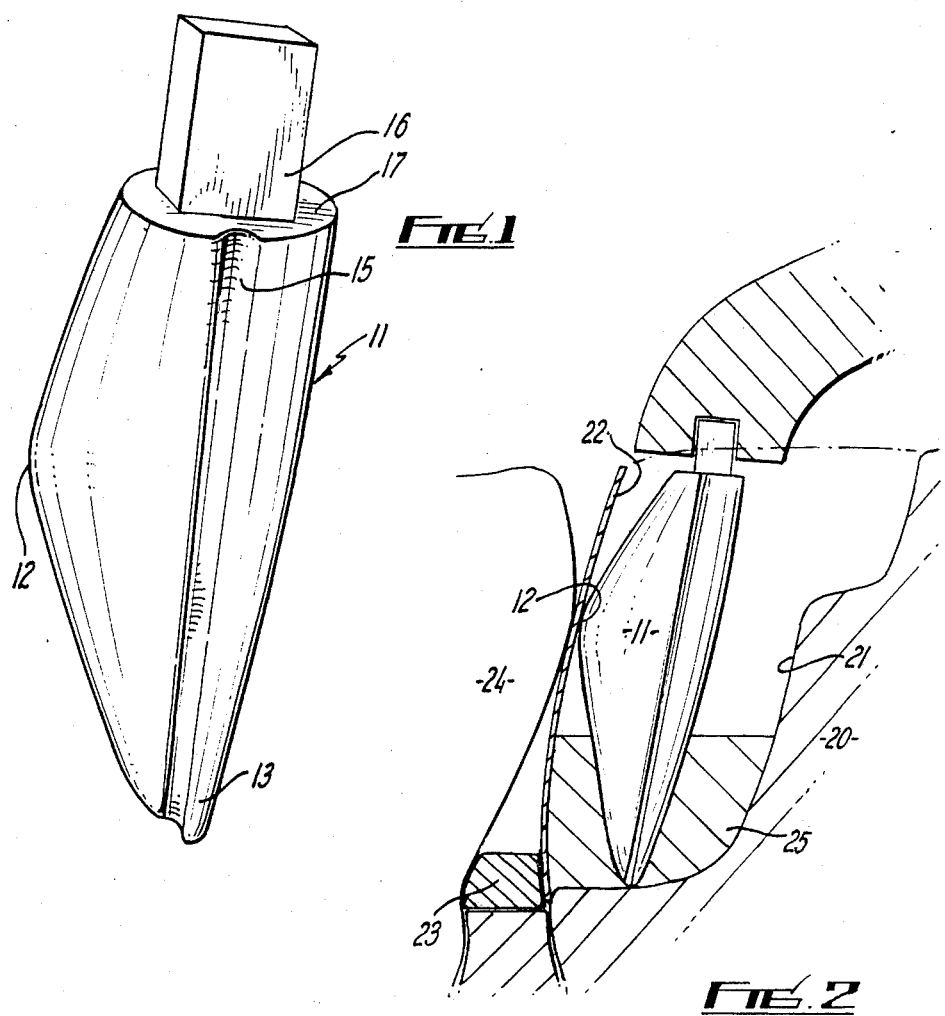
FIG.1
FIG.2
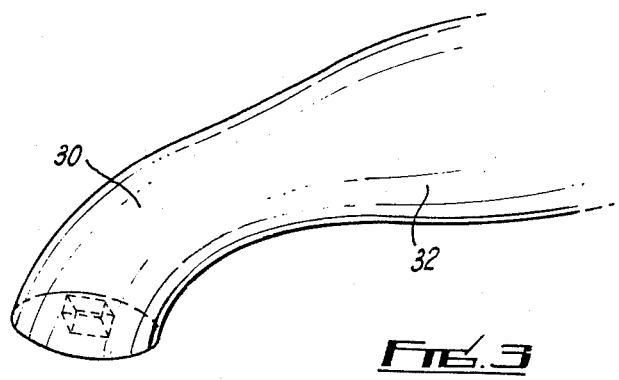
FIG.3

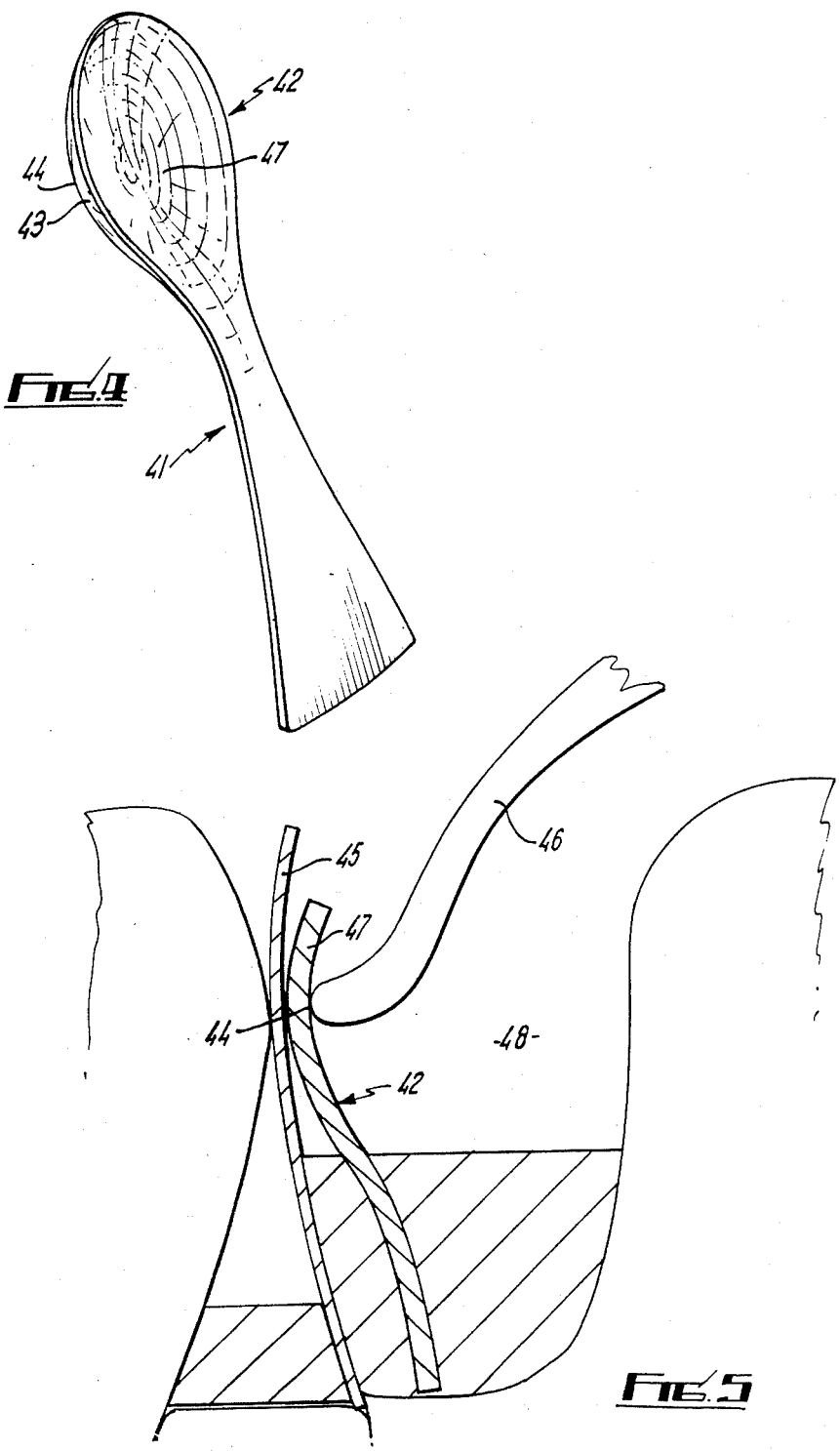

TOOTH RESTORATION AND MEANS FOR USE THEREIN

The invention concerns tooth restoration, and has more particular reference to a contact point forming means for use in relation thereto.

Whilst the use of composite resins in tooth restoration is known, difficulties are experienced in certain regards, one being the creation of a tight, intimate and correctly shaped contact with the approximal surface of the adjacent tooth. In the case of a conventional dental amalgam, the viscosity thereof is sufficient to push a matrix band into position and maintain such band in contact with an adjacent tooth towards which the relevant part of such band is displaced by the packed amalgam, but the viscosity of composite resins is such that physical displacement by the resin is not possible.

The primary purpose of the invention is to provide a means for locating and maintaining the relevant part of the matrix band in intimate surface contact with the approximal surface of the adjacent tooth such that the requisite contact point might exist in completion of the restoration.

According to one aspect of the present invention there is proposed a dental inclusion for insertion in an interproximal cavity to form a contact point with an adjacent tooth and which comprises a preformed body having a profiled outer surface thereto, the said surface including a knuckle for engagement with the said adjacent tooth, to define the contact point aforesaid.

According to a preferred feature of the invention the said profiled surface comprises an arcuately convex surface which defines the said contact point.

According to a further feature, the contact point comprises a wear resistant insert set in said profiled surface.

According to a still further feature of the invention, the body includes support means thereon to receive a hand instrument into engagement therewith.

Another problem met with in composite resin restorations, and in particular in connection with resins the setting of which is initiated by light emission of a particular wavelength, is that of difficulty in suitably illuminating resin in deep restorations, the difficulty presently being met by introducing multiple successive layers of resin and setting such layers individually.

It is a supplementary object of the invention to provide a means for facilitating illumination, and thereby allow of the setting at greater distance from the resin surface than has previously been possible.

Thus, according to another aspect of the invention the preformed body is of a transparent or translucent material.

The invention will now be described further, by way of example only, with reference to the accompanying drawings illustrating one embodiment thereof and in which:

FIG. 1 shows a first embodiment of the invention and shows a contact-point-forming inclusion in perspective view;

FIG. 2 is a diagrammatic view illustrating the manner of usage of the inclusion shown in FIG. 1;

FIG. 3 is a diagrammatic view, partly broken away and drawn to a different scale, of one form of instrument for use in handling the inclusion shown in FIG. 1;

FIG. 4 is a diagrammatic perspective view of a second embodiment of the invention; and FIG. 5 is a view corresponding to FIG. 2 and illustrates the manner of usage of the inclusion illustrated in FIG. 4.

Referring now to FIG. 1 of the drawings, a contact-point forming-inclusion for use in tooth restoration involving composite resin materials comprises an elongate body 11 of generally tapered form and of generally oval transverse cross-section.

The inclusion is for use in filling an interproximal cavity in a tooth, and that part of the surface of the body which will face outwardly of the cavity and towards the adjacent tooth is of convex form to define a knuckle 12 at the intended contact point.

If desired, the lower end 13 of body 11 may be provided with a localised lateral enlargement to form a foot, not shown.

One or more retention/venting grooves 15 are provided longitudinally of the body 11 and in positions remote from the knuckle 12, whilst a post 16 extends from the top face 17 of the body, releasably to receive a dental instrument.

Whilst the inclusion may be made from a variety of materials, the preferred material of choice is a resinous or vitreous material, such as Bis GMA (Bowen's Resin) or glass, the light transmission characteristics thereof being relevant to a purpose hereafter to be explained.

In use of the inclusion of FIG. 1, see now FIG. 2, a lesion in an existing tooth 20 is enlarged to give an interproximal cavity 21, and a matrix band 22 is applied to the tooth in conventional manner, a wedge 23 having been positioned between the tooth 20 under treatment and the next adjacent tooth 24 at that side thereof facing the cavity 21, in accordance with standard practice.

A first fill 25 of composite resin is applied to the cavity 21 and the body 11 is introduced into the unset resin, the lower end of the body resting on the bottom of the cavity 21 (or on resin existing therein) and the body 11 being manually held in a position wherein the knuckle 12 not only engages the matrix band 22 but also displaces the same towards the adjacent tooth, with the knuckle 12 occupying a position in which it will contact the adjacent tooth on removal of the matrix band 22 and wedge 23. Displacement of the matrix band 22 so that the knuckle 12 can assume its requisite position is effected by applying pressure through a hand instrument having a socket engageable with the post 16 on the body 11. In an alternative arrangement a female socket is provided on the body to receive a male formation on the hand instrument. The composite resin is then subjected to illumination to initiate setting thereof, and the body 11 is held in position until the resin has set. The hand instrument is then disengaged from the post 16 and such post is severed from the body, either immediately or at a later stage in the restoration.

The remainder of the cavity 21 is filled with composite resin and setting of such resin is initiated by illumination, in the usual way.

On completion of the restoration the matrix band 22 and the wedge 23 are removed, the two adjacent teeth assuming a natural relative disposition with knuckle 12 on the inclusion 11 now firmly positioned in tooth 20 making contact with the next adjacent tooth 24.

Whilst it is preferred that the inclusion be transparent, thus to provide a light transmission path for a reason hereafter to be explained, in its broadest sense the invention also contemplates the use of inclusions wholly or partially of a non-transparent material.

One form of hand instrument for use in positioning the inclusion in the tooth cavity is shown diagrammatically in FIG. 3, and will be seen to comprise an angular rod 30 which terminates in a socket 31 dimensioned for engagement with the upstanding post 16 on the top face 17 of body 11, there being a handle 32 provided coaxially of the rod to facilitate manipulation of the instrument.

Alternative forms of hand instrument, not illustrated, include such as tweezers or forceps having opposing contact elements on the ends of the respective limbs thereof, the said contact elements each being of rectilinear profile and being cooperable to define a socket for engagement with the upstanding post on the inclusion and means being provided, if desired, to lock the contact elements in clamping relationship with the post.

In a particularly advantageous form of hand instrument the contact elements are mounted at the ends of respective tweezer or forceps arms of bowed configuration, thus to minimise the extent to which the inclusion is masked from view and to facilitate illumination of the composite resin in the region of the inclusion.

A second embodiment of the invention and its manner of usage are shown in FIGS. 4 and 5. Thus, referring now to FIG. 4, a dental inclusion for use in creating a contact point in an interproximal restoration using composite resin comprises an elongate body 41 having a convexo-concave formation 42 at one end, the convex outer face 43 of such formation defining a knuckle 44 which, in use of the inclusion, constitutes a contact point. The body is of a rigid material acceptable for use in dentistry and will, for reasons hereafter to be explained, preferably be capable of transmitting light energy. Generally the elongate body will be thin and of constant thickness, but it may be of any form fitted to the purpose involved. Typically, the inclusion shown in FIG. 4 will have a thickness and a transverse dimension both of which lie between 1 and 3 mm, whilst the length of the inclusion will be between 2 and 5 mm.

The embodiment shown in FIG. 4 will be used in analogous manner to that of FIG. 1, but in this instance the body is held in position against the matrix band 45 by an instrument 46 which simply bears on the inclusion in the region of the concavity 46 of the convexo-concave formation 42, the loading applied through instrument 42 being such as to displace the matrix band 45 into contact with the adjacent tooth. As before, the inclusion is held in position until the first fill of composite resin present in the cavity 47 is set, the lower end of the inclusion being supported by the bottom of the cavity and, on setting of the resin, serving to hold the inclusion in position, with the concavo-convex formation in pressure contact with the matrix band, on removal of the instrument 46.

As has previously been indicated, conventional composite resins as used in dentistry are set by illuminating the same with light of an appropriate wavelength, but difficulty is experienced in satisfactorily initiating the setting of resin at distances from the resin surfaces in excess of a particular figure. In order to avoid the difficulty, it is usual to introduce multiple successive layers of resin and to initiate the setting in each such layer before the introduction of the next layer.

It has been found that use of inclusions of the kind hereinproposed does provide means whereby initiating of the setting of the resin is made possible at distances from the resin surface in excess of those at which initiation of setting has previously been possible.

It is therefore proposed, in accordance with a second aspect of the invention that the inclusion as aforesaid be wholly or partly of a light transmitting material, such that, on direct illumination of the free surface of the resin and/or that part of the inclusion extending from such free surface, the inclusion will serve to transmit such illumination to regions of the composite resin that it will increase the degree of cure above that which would occur in the absence of the inclusion.

In the case of the embodiment of FIG. 1, the preferred material of choice from which the inclusion is produced is said to be a resinous or vitreous material, and in accordance with the second aspect of the invention such material will be transparent to light or other emissions of wavelengths appropriate to the initiation of the setting of composite resins as used in dentistry.

As to the FIG. 4 embodiment, again the inclusion will be of a suitably transparent material, the body being an integral element, homogeneous in character, or an assembly of parts joined together to give a rigid element. In the latter instance the convexo-concave formation may be glass whilst the remainder of the inclusion may be of a transparent synthetic material.

Thus, the second aspect of the invention involves the utilisation of an inclusion of a transparent material for the express purpose of facilitating illumination for setting purposes. However, whilst in the context of the first aspect of the invention the inclusion has a knuckle for use in the creation of a contact point, it is not necessary according to the second aspect that such a knuckle be present.

In accordance with the second aspect of the invention it is necessary only that the inclusion transmit energy at wavelengths appropriate to initiate setting of the composite resin, and the geometrical form of the body may vary appreciably according to the nature of the cavity to be filled. Thus, the body may comprise a base of circular or other form and a post extending upwardly therefrom, the base being dimensioned to seat on the bottom of the cavity, or on resin existing thereon, and the post serving to transmit light energy downwardly to the base, the light energy passing from the post and base to the surrounding resin. In another arrangement the body is of elongate form and of reducing transverse dimension towards its lower end, such body terminating in a foot for seating on the bottom of the prepared cavity or on resin existing in such cavity. In a still further embodiment, the body is of flattened Y-form, and again has a foot whereby the same is supported.

Other forms of body may be preferred in some circumstances.

In conjunction with the second aspect of the invention, the inclusion, whether the same includes the knuckle of the first aspect of the invention or otherwise, may be held in position by an instrument through which light is transmitted directly thereto, the resin surface being directly illuminated or not as preferred.

In such circumstances the instrument as shown in FIGS. 3 and 5 will have light transmitting characteristics, as, for example, by the incorporation of light transmitting fibres.

The invention is not limited to the exact features of the embodiments hereindisclosed, since alternatives will readily present themselves to one skilled in the art.

Thus, for example, for the post provided on the top of the inclusion of FIG. 1 there may be substituted a recess, the hand instrument providing a complementary male formation for cooperation therewith.

In a further alternative, the embodiment shown in FIG. 1 will be modified by the inclusion of an insert of a wear resistant material, the insert having an arcuately profiled outer surface which defines the contact point and such insert being applied to the inclusion prior to the same being located in the cavity.

Whilst the invention has been disclosed in the context of composite resins the setting of which is initiated by illumination, and the second aspect of the invention is concerned solely with such resins, the contact point forming inclusions of the invention may also be used in the context of chemically cured composite resins, if desired.

It will be appreciated that the composite resin, whether of the kind the setting of which is initiated by illumination by an appropriate emission or of the chemically curing kind, will form a mechanical bond with the inclusion.

According to the chemical characteristics of the material of the inclusion as relative to those of the composite resin, there may also be a chemical bond between such inclusion and the resin.

The invention is not restricted to the exact forms of inclusion herein described and illustrated, since alternatives will readily present themselves to one skilled in the art.

Thus, for example, the convexo-concave formation of the embodiment shown in FIG. 4 may, if desired, be provided intermediate the ends, rather than at an end, of the elongate body, the formation being in offset disposition relative to the centre of such body thus to allow of the selective insertion of the inclusion into the cavity with the longer or shorter length directed towards the floor thereof according to the depth of the cavity.

The profile of that surface of the inclusion remote from the knuckle forming surface thereof is not critical, and in the case of the embodiment shown in FIG. 4 may be other than concave, being shaped to receive a hand instrument or not as desired.

I claim:

1. A dental inclusion for insertion in an interproximal cavity of a tooth for restoration to form a contact point with an adjacent tooth wherein a matrix band with wedge are employable by applying the matrix band both to the tooth having said cavity and between the tooth having said cavity and the adjacent tooth with the wedge being positioned both between the tooth having said cavity and the adjacent tooth and between the matrix band and the adjacent tooth generally during the restoration, comprising a rigid preformed body having a profiled outer surface with that part of said profiled surface facing outwardly from said cavity and towards the adjacent tooth being of convex form to define a knuckle for engagement with the adjacent tooth which defines said contact point whereby on completion of the tooth restoration the matrix bond and the wedge are to be removed, and the restored tooth and the adjacent tooth will assume a natural relative disposition toward each other with said knuckle on the inclusion in firm position in the restored tooth and generally in contact with the adjacent tooth.

2. A dental inclusion as claimed in claim 1, wherein said profiled surface comprises an arcuately convex surface which defines said contact point.

3. A dental inclusion as claimed in claim 1 or 2, wherein said contact point comprises a wear resistant insert set in said profiled surface.

4. A dental inclusion as claimed in claim 1, wherein the body includes support means thereon to receive a hand instrument into engagement therewith.

5. A dental inclusion as claimed in claim 4, wherein the support means includes a male formation integral with and extending outwardly from the body.

6. A dental inclusion as claimed in claim 1 or 4, wherein the body is of generally elongate cylindrical form, and said knuckle is positioned intermediate to the ends of the body.

7. A dental inclusion as claimed in claim 1, wherein the body is elongate and comprises a portion of convexo-concave form.

8. A dental inclusion as claimed in claim 7, wherein the convexo-concave portion of the body is provided in spaced apart disposition relative to the longitudinal extremities of such body.

9. A dental inclusion as claimed in claim 1, wherein the preformed body comprises a material transparent to resin setting emissions.

10. A dental inclusion as claimed in claim 1, wherein the preformed body comprises a resinous or vitreous material.

11. A dental inclusion as claimed in claim 1, further including a venting formation therein.

12. A dental inclusion comprising a preformed body part having a base thereto adapted and arranged to support the body part in upstanding disposition in a tooth cavity, the body part being of a material suitable for use in dentistry and of a kind capable of transmitting electro-magnetic or other radiations appropriate to initiation of the setting of composite resins of the kind used in the field of dentistry.

13. A dental inclusion as claimed in claim 12, wherein the dental inclusion is for insertion in an interproximal cavity of a tooth for restoration to form a contact point with an adjacent tooth wherein a matrix band with wedge are employable by applying the matrix band both to the tooth having said cavity and between the tooth having said cavity and the adjacent tooth with the wedge being positioned both between the tooth having said cavity and the adjacent tooth and between the matrix band and the adjacent tooth generally during the restoration, wherein the body part has a profiled outer surface with that part of said profiled surface facing outwardly from said cavity and towards the adjacent tooth being of convex form to define a knuckle for engagement with said adjacent tooth which defines said contact point and whereby on completion of the tooth restoration the matrix bond and the wedge are to be removed, and the restored tooth and the adjacent tooth will assume a natural relative disposition toward each other with said knuckle on the inclusion in firm position in the restored tooth and generally in contact with the adjacent tooth.

14. In the restoration of a tooth having an interproxal cavity, the method of forming a contact point with an adjacent tooth which includes the steps of engaging a matrix band about the tooth to be restored, locating a profiled dental inclusion in the cavity and inwardly of the matrix band, the inclusion having a contact-point or knuckle-forming surface and said surface facing towards the said adjacent tooth, loading the dental inclusion within the cavity laterally into pressure-engagement with the matrix band to displace the band towards and into contact with the adjacent tooth, in a position in register with intended contact point, introducing composite dental resin in an amount sufficient at least partially to fill the cavity with the inclusion embedded in such resin and initiating setting or curing thereof, the inclusion being maintained in pressure contact with the matrix band until the composite resin is set or cured sufficiently to hold the inclusion in position in the cavity.

15. In the restoration of a tooth having a cavity therein, the method of initiating curing or setting of light-sensitive composite resin which includes the steps of at least partially embedding a light transmitting element in uncured composite resin in the cavity and illuminating the resin through the said element.

16. The method as claimed in claim 15, wherein the light transmitting element is located in the cavity and composite resin is applied to the cavity so as at least in part to cover the element.

17. In the method as claimed in claim 14 the step of engaging a formation on the dental inclusion with a complementary shaped element on a hand instrument and loading the inclusion into pressure engagement with the matrix band through such hand instrument.

18. In the method as claimed in claim 17, the step of utilising a hand instrument adapted and arranged to permit of the ready illumination of the inclusion.

* * * * *